US009784676B2

(12) United States Patent
Luo et al.

(10) Patent No.: US 9,784,676 B2
(45) Date of Patent: Oct. 10, 2017

(54) SUBSTRATE INSPECTION DEVICE AND SUBSTRATE INSPECTION METHOD

(71) Applicants: BOE TECHNOLOGY GROUP CO., LTD., Beijing (CN); HEFEI XINSHENG OPTOELECTRONICS TECHNOLOGY CO., LTD., Hefei, Anhui (CN)

(72) Inventors: Peng Luo, Beijing (CN); He Wang, Beijing (CN); Xin Fang, Beijing (CN); Jiajia Peng, Beijing (CN); Xiang Liu, Beijing (CN)

(73) Assignees: BOE TECHNOLOGY GROUP CO., LTD. (CN); HEFEI XINSHENG OPTOELECTRONICS TECHNOLOGY CO., LTD. (CN)

( * ) Notice: Subject to any disclaimer, the term of this patent is extended or adjusted under 35 U.S.C. 154(b) by 9 days.

(21) Appl. No.: 14/739,102

(22) Filed: Jun. 15, 2015

(65) Prior Publication Data
US 2016/0258866 A1 Sep. 8, 2016

(30) Foreign Application Priority Data
Mar. 2, 2015 (CN) .......................... 2015 1 0093266

(51) Int. Cl.
*G01N 21/956* (2006.01)
*G01N 21/59* (2006.01)

(52) U.S. Cl.
CPC ........... *G01N 21/59* (2013.01); *G01N 21/956* (2013.01); *G01N 2201/06113* (2013.01)

(58) Field of Classification Search
CPC .... G01B 11/02; G01B 11/046; G01N 21/956; G01N 2021/95676
(Continued)

(56) References Cited

U.S. PATENT DOCUMENTS 6,538,795 B2 * 3/2003 Tateno ................. G01N 21/956
359/285
7,271,904 B2 * 9/2007 Jung ..................... G02F 1/1339
118/410
(Continued)

FOREIGN PATENT DOCUMENTS

CN 101568797 A 10/2009
CN 102080951 A 6/2011
(Continued)

OTHER PUBLICATIONS

Office Action in Chinese Patent Application No. 201510093266.X, dated Nov. 1, 2016.

*Primary Examiner* — Hoa Pham
(74) *Attorney, Agent, or Firm* — Brooks Kushman P.C.

(57) ABSTRACT

A substrate inspection device includes a laser emitting unit, arranged at one side of a transmission device, and configured to emit a laser beam to each substrate to be inspected on the transmission device when the substrate to be inspected is moved to an inspection position; a laser receiving unit, arranged at the other side of the transmission device, and configured to receive the laser beam transmitted through the substrate to be inspected; and a calculation unit, configured to calculate transmissibility of the laser beam relative to the substrate to be inspected based on an intensity of the laser beam emitted by the laser emitting unit and an intensity of the laser beam received by the laser receiving unit, and determine whether a line width of a black matrix in the substrate to be inspected is within a predetermined range of the line width based on the transmissibility.

18 Claims, 4 Drawing Sheets

(58) Field of Classification Search
USPC .................. 356/237.1–237.5, 636, 635, 639
See application file for complete search history.

(56) References Cited

U.S. PATENT DOCUMENTS

| | | | | |
|---|---|---|---|---|
| 7,793,252 | B2* | 9/2010 | Kotani | ................ G03F 7/70433 |
| | | | | 430/5 |
| 2005/0126679 | A1* | 6/2005 | Kim | ...................... G02F 1/1339 |
| | | | | 156/64 |
| 2009/0225390 | A1 | 9/2009 | Lin et al. | |
| 2012/0113246 | A1* | 5/2012 | He | ....................... G01N 21/956 |
| | | | | 348/87 |
| 2014/0132760 | A1* | 5/2014 | Lin | ........................ G01B 11/02 |
| | | | | 348/136 |

FOREIGN PATENT DOCUMENTS

| | | |
|---|---|---|
| CN | 103364374 A | 10/2013 |
| JP | 2000-227311 A | 8/2000 |

* cited by examiner

A line width of a black matrix

SUBSTRATE INSPECTION DEVICE AND SUBSTRATE INSPECTION METHOD

CROSS REFERENCE OF RELATED APPLICATION

The present application claims the priority of Chinese patent application No. 201510093266.X filed on Mar. 2, 2015, the disclosure of which is incorporated herein by reference.

TECHNICAL FIELD

The present disclosure relates to a technical field of displaying, and in particular to a substrate inspection device and a substrate inspection method.

BACKGROUND

Conventionally, micro black defects and white defects on a color film (CF) substrate are generally inspected by a total inspection machine, which monitors a defect trend of all kinds of products. The inspection of a black matrix is a first process in color film processes. As illustrated in FIG. 1, main functions of the black matrix lie in:

1. as being a non-transmissible zone of light, distinguishing RGB (red, green, blue) areas; and
2. upon designing a product, it is required to consider affections on chrominance by a size of a width (line width) of a black matrix area, wherein the defects such as overlapping of the RGB areas or light leaking may arise if the line width is small, and the contrast and the chrominance may be caused to be varied if the line width is large.

Thus, during manufacturing of a color film, the inspection of the line width of the black matrix is an important process. Conventionally, the inspection of the line widths of the black matrices by the total inspection machine may be merely implemented by marking lines and then measuring by review lenses. During the measurement, it is required to stop the device which is transmitting color film substrates. Thus, the time duration for measuring is long, and it is difficult to inspect the line width of the black matrix in each color film substrate. Moreover, if the device is stopped for inspecting, a takt time of a product line of the black matrix will be extended, which may affect productivity of the whole color film substrate production line. On the other hand, if the line widths of the black matrices are inspected by total sampling, it will take a long time, and it is difficult to achieve a real-time monitoring, thereby leading to a higher risk of yield loss.

SUMMARY

A technical problem to be solved by the present disclosure is how to continuously inspect the line width of the black matrix in the substrate, so that it is not necessary to stop the device transmitting the black matrix, while the inspecting precision and the response speed may be improved.

For the above object, the present disclosure provides a substrate inspection device including: a calculation unit, a laser emitting unit, and a laser receiving unit arranged in correspondence with the laser emitting unit, wherein the laser emitting unit is arranged at one side of a transmission device, and configured to emit a laser beam to each substrate to be inspected on the transmission device when the substrate to be inspected is moved to an inspection position;

the laser receiving unit is arranged at the other side of the transmission device, and configured to receive the laser beam transmitted through the substrate to be inspected; and the calculation unit is configured to calculate transmissibility of the laser beam relative to the substrate to be inspected based on an intensity of the laser beam emitted by the laser emitting unit and an intensity of the laser beam received by the laser receiving unit, and determine whether a line width of a black matrix in the substrate to be inspected is within a predetermined range of the line width based on the transmissibility.

Alternatively, the calculation unit is further configured to determine whether the transmissibility is within a predetermined range of the transmissibility. If not, the calculation unit determines that the line width of the black matrix in the substrate to be inspected is not within a predetermined range of the line width. If yes, the calculation unit determines that the line width of the black matrix in the substrate to be inspected is within a predetermined range of the line width.

Alternatively, the predetermined range of the line width is obtained by inspecting a predetermined position of a standard substrate by a user.

Alternatively, the predetermined position is same as the inspecting position of the substrate to be inspected.

Alternatively, the calculation unit is further configured to convert the transmissibility into the line width of the black matrix in the substrate to be inspected, and determine whether the line width of the black matrix is within the predetermined range of the line width.

Alternatively, the line width of the black matrix=$A\times(-\log$ (a value of the transmissibility))+$B$, wherein both $A$ and $B$ are constants.

Alternatively, the substrate inspection device further includes:

a setting unit, configured to set the constants $A$, $B$ and/or the predetermined range of the line width according to a received instruction.

Alternatively, the substrate inspection device further includes:

an alert unit, configured to send an alert message when the calculation unit determines that the line width of the matrix in the substrate to be inspected is not within the predetermined range of the line width.

Alternatively, the substrate inspection device further includes:

a control unit, configured to control movements of the laser emitting unit and the laser receiving unit based on an exposing area of the substrate to be inspected, and control a position where the laser emitting unit emits the laser.

Alternatively, the control unit is further configured to be connected to the transmission device and the calculation unit, and control the transmission device to stop moving when the calculation unit determines that the line width of the black matrix in the substrate to be inspected is not within the predetermined range of the line width.

Alternatively, when the substrate to be inspected includes a plurality of exposed areas, the control unit controls the laser emitting unit and the laser receiving unit to reciprocate in a direction perpendicular to a direction in which the transmission device moves, and control the laser emitting unit to emit the laser beam upon moving to the predetermined position in each of the plurality of exposed areas in the substrate to be inspected, and the calculation unit calculates the transmissibility of each of the plurality of exposed areas, and calculates the transmissibility of the substrate to be inspected based on the transmissibility of each of the plurality of exposed areas.

Alternatively, when the substrate to be inspected includes four exposed areas, the control unit controls the laser emitting unit and the laser receiving unit to move to any three exposed areas in the substrate to be inspected, and control the laser emitting unit to emit the laser beam upon moving to the predetermined position in each of the three exposed areas, the calculation unit calculates the transmissibility of each of the plurality of exposed areas, and calculates the transmissibility of the substrate to be inspected based on the transmissibility of each of the three of exposed areas.

The present disclosure further provides a substrate inspection method including:

emitting a laser beam to a substrate to be inspected at one side of the substrate to be inspected;

receiving the laser beam transmitted through the substrate to be inspected at the other side of the substrate to be inspected; and calculating transmissibility relative to the substrate to be inspected based on the emitted laser beam and the received laser beam, and determines whether a line width of a black matrix in the substrate to be inspected is within a predetermined range of the line width based on the transmissibility.

In the above technical solutions, the laser emitting unit and the laser receiving unit are provided at two sides of the transmission device respectively, and the transmissibility of the laser relative to the substrate may be calculated by irradiating the substrate by the laser beam, so that the line width of the black matrix in the substrate may be calculated based on the transmissibility, and thus it is determined whether the line width of the black matrix meets the requirement. Thus, the line width of the matrix in each substrate to be inspected on the transmission device may be inspected without stopping the transmission device, and the line width of the black matrix may be calculated in a prompt and precise manner based on the transmissibility.

BRIEF DESCRIPTION OF THE DRAWINGS

The features and advantages of the present disclosure may be more apparent by referring to drawings which are illustrative only, and should not be considered as limiting the scope of the present disclosure, wherein.

DETAILED DESCRIPTION

In the following, the present disclosure will be further explained in details by associating drawings and embodiments, so that the above objects, features and advantages of the present disclosure may be more obvious. It is noted that the embodiments and the features in the embodiments can be combined with each other if possible.

In the following, numeric details are recited for further explaining the present disclosure; the present disclosure may also be implemented with means other than those illustrated herein. Thus, the protection scope of the present disclosure is not limited to the following specific embodiments.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "a/an" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

Figure 1:
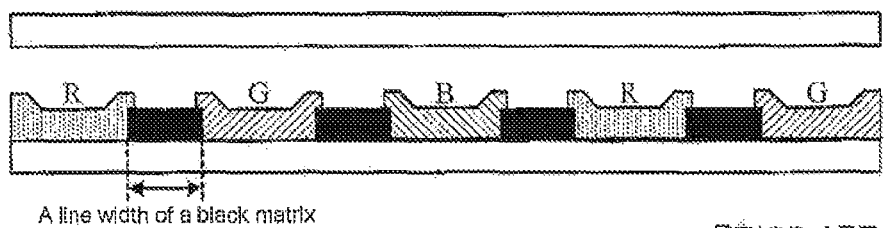
FIG. 1 illustrates a black matrix in a conventional color film substrate.
Figure 2:
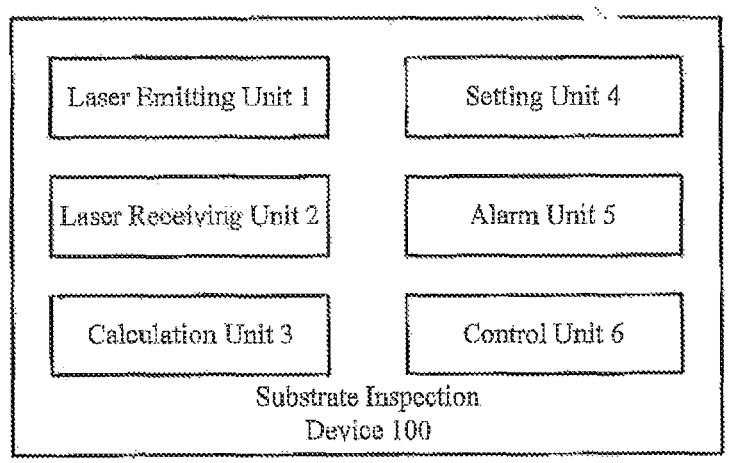
FIG. 2 is a block diagram of a substrate inspection device according to an embodiment of the present disclosure.
Figure 3:
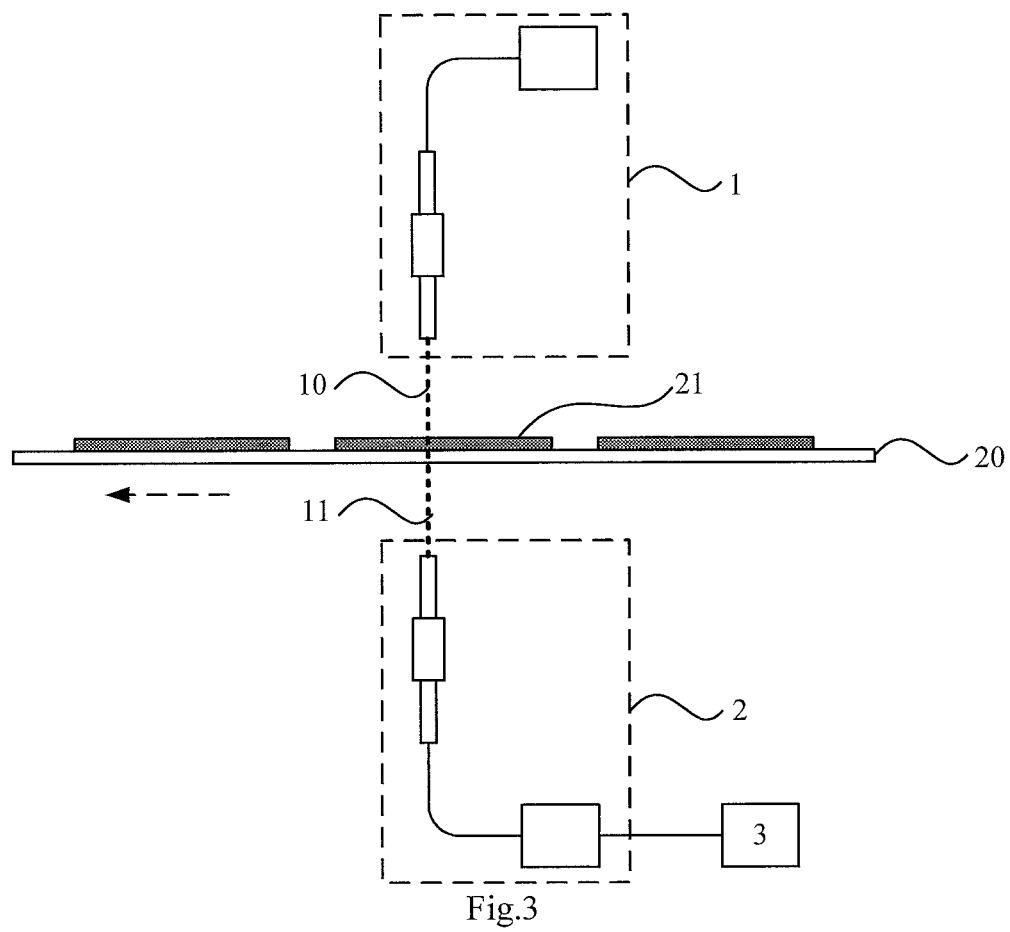
FIG. 3 is a side view of a structure of the substrate inspection device according to an embodiment of the present disclosure.

As illustrated in FIGS. 2 and 3, a substrate inspection device 100 according to the embodiment of the present disclosure includes a calculation unit 3, and a laser emitting unit 1 and a laser receiving unit 2 arranged in correspondence with each other.

Figure 4:
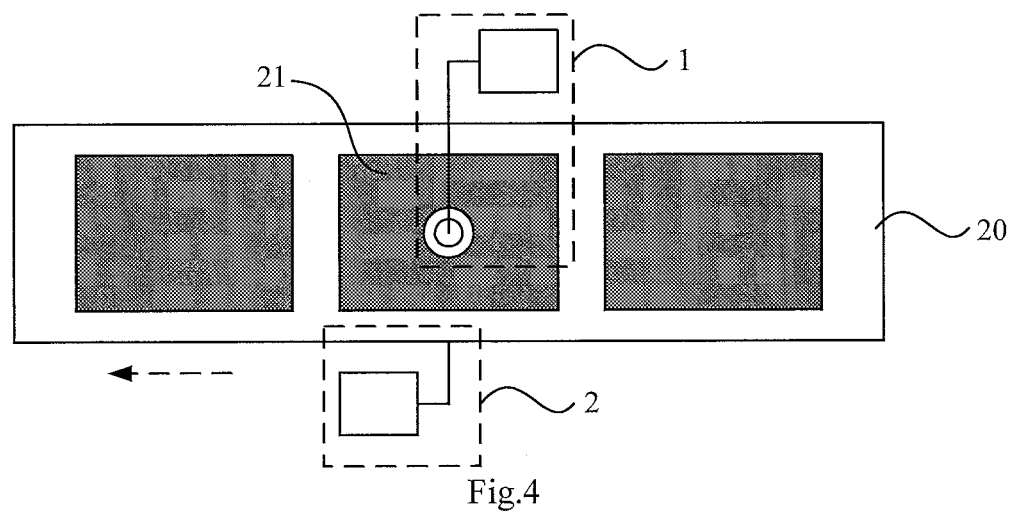
FIG. 4 is a top view of a structure of the substrate inspection device according to an embodiment of the present disclosure.

The laser emitting unit 1 is arranged at one side of a transmission device 20 which may be transparent, and configured to emit a laser beam to each substrate 21 to be inspected on the transmission device 20 when the substrate 21 to be inspected is moved to an inspection position (for example, a predetermined position on the substrate 21 to be inspected is moved to a position directly under the laser emitting unit);

The laser receiving unit 2 is arranged at the other side of the transmission device 20, and configured to receive the laser beam transmitted through the substrate 21 to be inspected;

As illustrated in FIGS. 3 and 4, the laser emitting unit 1 may be arranged at a position above the transmission device 20, and the laser receiving unit 2 may be arranged at a position under the transmission device 20; the calculation unit 3 may be connected to the laser emitting unit 1 and the laser receiving unit 2 respectively.

The calculation unit 3 is configured to calculate transmissibility of the laser beam relative to the substrate to be inspected based on an intensity of the laser beam 10 emitted by the laser emitting unit 1 and an intensity of the laser beam 12 received by the laser receiving unit 2, and determine whether a line width 31 of a black matrix in the substrate 21 to be inspected is within a predetermined range of the line width based on the transmissibility.

Figure 5:
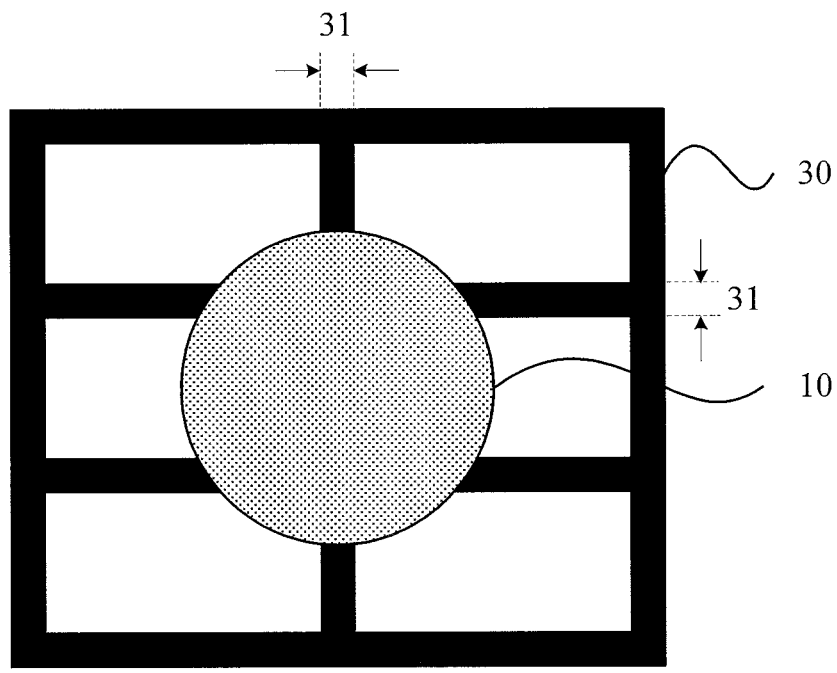
FIG. 5 illustrates a laser irradiating on a black matrix according to an embodiment of the present disclosure.

As illustrated in FIG. 5, the line widths of the black matrices in a substrate 21 to be inspected (for example, a color film substrate) are substantially same. When the emitted laser beam 10 irradiates on the substrate 21 to be inspected, the black matrix 30 may shield the emitted laser beam 10. For different substrates 21 to be inspected on the transmission device 20, the structures of the black matrices 30 on the predetermined positions on the substrates 21 to be inspected are generally same with each other, and the difference merely lies in the line widths 31 of the black matrices. The larger the line width 31 of the black matrix is, the wider the black matrix 30 is, the more shielding of the emitted laser beam 10 is, and the lower the transmissibility relative to the substrate 21 to be inspected is. In other words, the transmissibility relative to the substrate 21 to be inspected is related to the line width 31 of the black matrix. Thus, the line width 31 of the black matrix may be calculated based on the transmissibility relative to the corresponding substrate 21 to be inspected.

The substrate 21 to be inspected is driven to move by the transmission device 20. Each time the substrate 21 to be inspected moves to the position under the laser emitting unit 1, the transmissibility relative to the substrate 21 to be inspected may be calculated by irradiating the laser beam, and thus the line width 31 of the black matrix in each substrate 21 to be inspected may be calculated based on the transmissibility. Then, it is determined whether the line width 31 of the black matrix obtained by calculating is within a predetermined range of the line width, and thus it may be determined whether the line width 31 of the black matrix in the substrate 21 to be inspected meets the requirement. The predetermined range of the line width may be determined by inspecting a predetermined position in a standard substrate (i.e. the position which is same as the inspection position in the substrate 21 to be inspected) by a user.

In this embodiment, it is not necessary for the substrate inspection device to stop the transmission device 20 during the inspection process, and thus the efficiency of the transmission device 20 is improved; and each of the substrate 21 to be inspected on the transmission device 20 may be inspected as the transmission device 20 moves, and thus the yield rate of the substrate 21 to be inspected is secured. Furthermore, since the transmissibility rigidly corresponds to the line width 31 of the black matrix, the line width 31 of the black matrix may be accurately calculated based on the transmissibility, so that it is accurately determined whether the substrate 21 to be inspected meets the requirement.

Alternatively, the calculation unit 3 is further configured to determine whether the transmissibility is within a predetermined range of the transmissibility. If not, the calculation unit determines that the line width 31 of the black matrix in the substrate 21 to be inspected is not within the predetermined range of the line width. If yes, the calculation unit determines that the line width of the black matrix in the substrate 21 to be inspected is within the predetermined range of the line width.

A person skilled in the art may understands that the calculation unit 3 may determine whether the line width 31 of the black matrix in the substrate 21 to be inspected is within the predetermined range of the line width directly by determining whether the transmissibility relative to the substrate 21 to be inspected is within the predetermined range of the transmissibility. Thus, the conversion is not required and the calculation may be implemented in a prompt manner.

Alternatively, the calculation unit 3 is further configured to convert the transmissibility into the line width 31 of the black matrix in the substrate to be inspected, and determine whether the line width 31 of the black matrix is within the predetermined range of the line width.

Alternatively, the line width 31 of the black matrix=A×(−log (the value of the transmissibility))+B, wherein both A and B are constants.

Since it is difficult for the laser beam to transmit the black matrix 30, the received laser 11 may be weak when the emitted laser beam 10 irradiates on the position dominated by the black matrices, so that the order of the magnitude of the transmissibility is very small, and it is difficult to implement the calculation. Moreover, it is difficult to intuitively show the user of the specific size of the line width 31 of the black matrix in the substrate 21 to be inspected by displaying the transmissibility. Thus, the transmissibility may be converted to the line width of the black matrix, specifically the exponential transformation may be made on the transmissibility to obtain a relatively large number, and then the line width 31 of the black matrix may be calculated based on the constants A and B.

Alternatively, the substrate inspection device further includes:

a setting unit 4 (not shown), which may be specified as a button, a switch, a virtual key or etc, and configured to set the constants A, B and/or the predetermined range of the line width according to an received instruction. Both constants A and B may be set by the user, and are related to the specific process of manufacturing the substrate 21 to be inspected.

Alternatively, the substrate inspection device may further include:

an alert unit 5 (not shown), configured to send an alert message when the calculation unit 3 determines that the line width 31 of the matrix in the substrate to be inspected is not within the predetermined range of the line width. Specifically, the alert unit may send an alert of sounding/lighting, for example, sounding an alarm and/or activating a red warning light. Alternatively, it may intuitively show the transmissibility and the line width 31 of the black matrix.

Alternatively, the substrate inspection device may further include:

a control unit 6 (not shown) which may be connected to the laser emitting unit 1 and the laser receiving unit 2, and configured to control movements of the laser emitting unit 1 and the laser receiving unit 2 according to an exposed area of the substrate 21 to be inspected, and control the position where the laser emitting unit 1 emits the laser beam. The control unit may be further connected to the transmission device 20 and the calculation unit 3, and control the transmission device 20 to stop moving when the calculation unit 3 determines that the line width 31 of the black matrix in the substrate 21 to be inspected is not within the predetermined range of the line width, so that an unqualified substrate 21 to be inspected may be removed.

Figure 6:
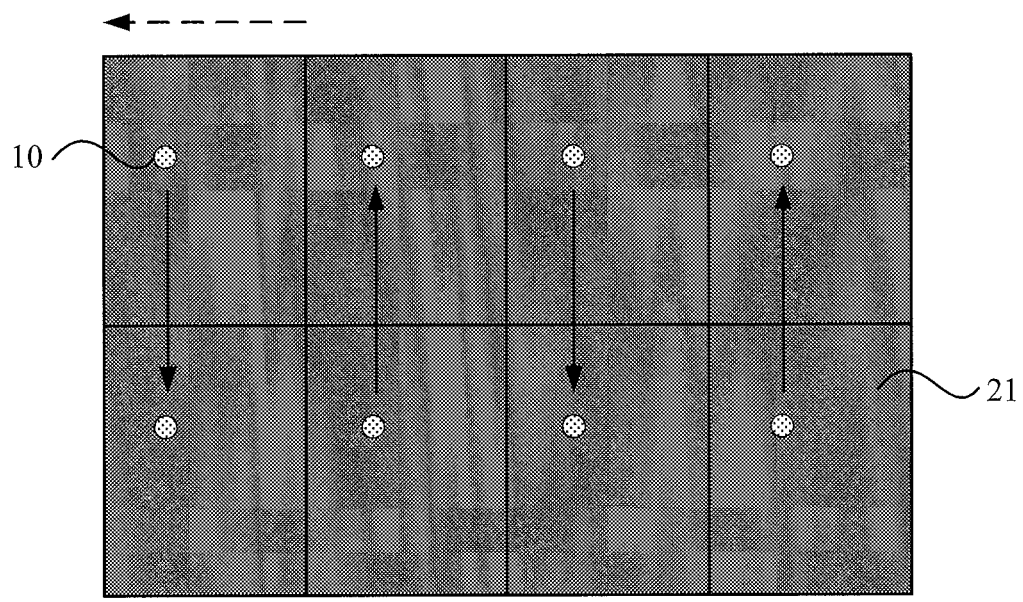
FIG. 6 illustrates an inspection of a plurality of exposed areas according to an embodiment of the present disclosure.

Alternatively, as illustrated in FIG. 6 (it is merely indicated by the emitted laser beam 10, and the laser emitting unit 1 is at a position corresponding to emit the laser 10), when the substrate 21 to be inspected includes a plurality of exposed areas, the control unit 6 may further control the laser emitting unit 1 and the laser receiving unit 2 to reciprocate in a direction (indicated by a arrow with a solid line) perpendicular to a direction (indicated by a arrow with a dotted line) in which the transmission device 20 moves, and control the laser emitting unit 1 to emit the laser beam upon moving to the predetermined position in each of the plurality of exposed areas in the substrate 21 to be inspected.

At this point, the calculation unit 3 calculates the transmissibility relative to each of the plurality of exposed areas, and calculates the transmissibility relative to the substrate 21 to be inspected based on the transmissibilities relative to the plurality of exposed areas.

If the substrate 21 to be inspected is large, it is necessary to divide the substrate 21 to be inspected into a plurality of areas and expose each of the plurality of areas, so that the black matrix 30 may be formed at each area. Due to slight differences among the exposing processes, the predetermined position at each exposed area may be continuously and respectively inspected when the substrate 21 to be inspected includes a plurality of exposed areas, so as to obtain the transmissibility relative to each exposing area, and then calculate the transmissibility relative to the substrate 21 to be inspected (for example, taking an average value) based on the transmissibilities relative to the plurality of the exposed areas. Thus, the more accurate value of the transmissibility relative to the substrate 21 to be inspected may be obtained.

The transmission speed of the transmission device 20 may be set based on the width of the exposing area. Generally the transmission speed may be set to be slow, while the laser emitting unit 1 may be set to be in a fast speed, so that the laser emitting unit 1 may promptly move to the predetermined position in each exposing area for inspecting during the movement of the transmission device 20. In fact, in order to be accurately moved to the predetermined position in each exposing area, the laser emitting unit 1 can be controlled such that an angle may exist between the movement direction of the laser emitting unit 1 and the movement direction of the transmission device 20. It should be noted that, during the movement of the laser emitting unit 1, the laser receiving unit 2 moves synchronously, and is being at the other side of the transmission device 20 and receiving the laser beam transmitted through the substrate 21 to be inspected all the time.

Alternatively, when the substrate 21 to be inspected includes four exposed areas, the control unit 6 controls the laser emitting unit 1 and the laser receiving unit 2 to move to any three exposed areas in the substrate to be inspected, and control the laser emitting unit 1 to emit the laser beam upon moving to the predetermined position in each of the any three exposed areas. At this point, the calculation unit 3 calculates the transmissibility relative to each of the plurality of exposed areas, and calculates the transmissibility relative to the substrate 21 to be inspected based on the transmissibility relative to each of the three exposed areas.

Figure 7:
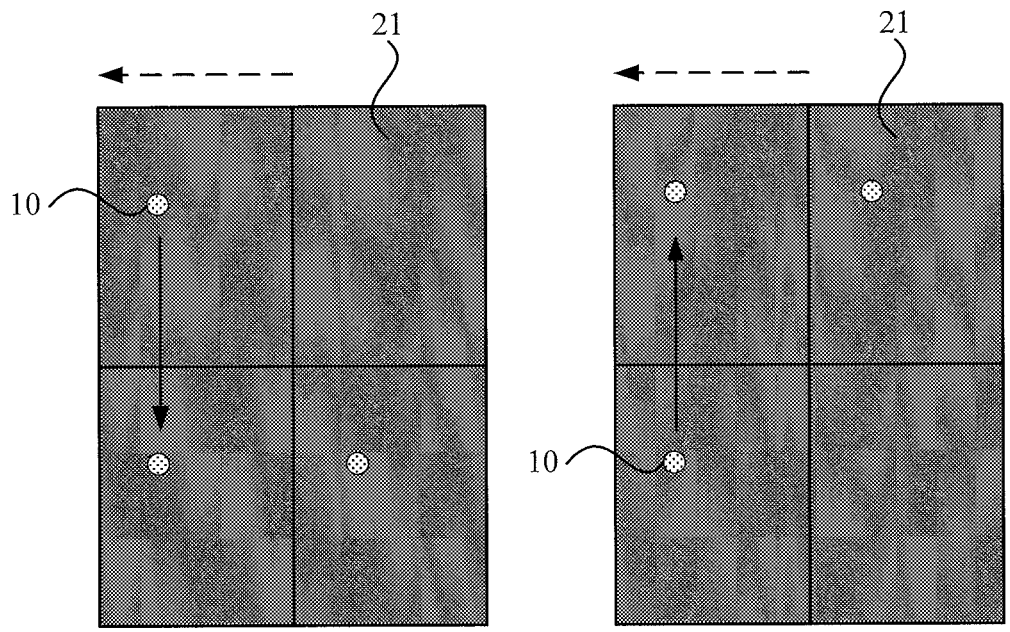
FIG. 7 illustrates an inspection of four exposed areas according to an embodiment of the present disclosure.

When there are a plurality of exposed areas (for example, four exposed areas) in the substrate 21 to be inspected, a relatively accurate value of the transmissibility relative to the whole substrate 21 to be inspected may be obtained by calculating the transmissibilities relative to three of the four exposed areas, so that the movements of the light emitting unit 1 and the light receiving unit 2 may be reduced. The inspection of two consecutive substrates 21 to be inspected on the transmission device 20 is illustrated in FIG. 7.

Figure 8:
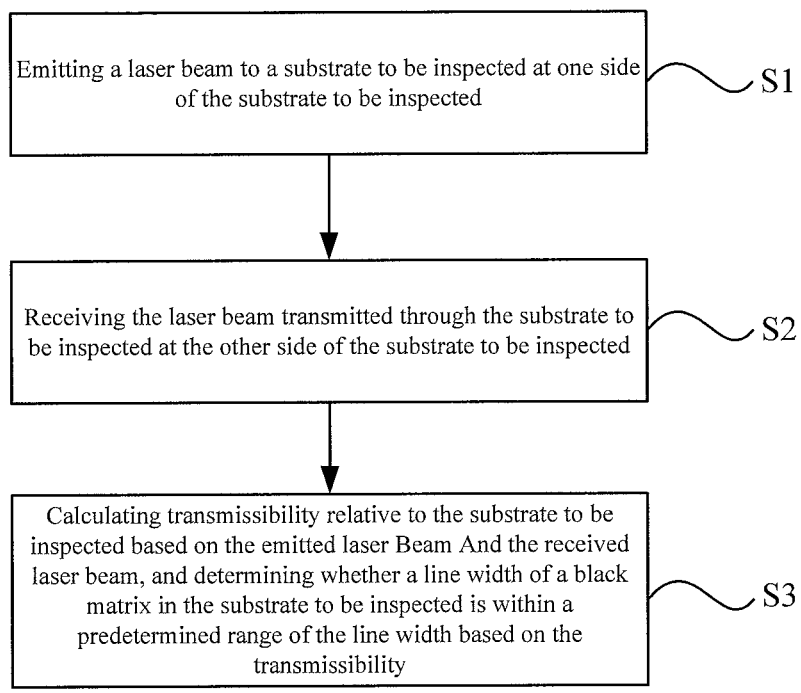
FIG. 8 is a flow diagram of a substrate inspection method according to an embodiment of the present disclosure.

As illustrated in FIG. 8, an embodiment of the present disclosure further provides a substrate inspection method, including:

step S1, emitting a laser beam 10 to a substrate 21 to be inspected at one side of the substrate 21 to be inspected;

step S2, receiving the laser beam 11 transmitted through the substrate 21 to be inspected at the other side of the substrate 21 to be inspected; and step S3, calculating transmissibility relative to the substrate 21 to be inspected based on the emitted laser beam 10 and the received laser beam 11, and determining whether a line width of a black matrix in the substrate to be inspected is within a predetermined range of the line width based on the transmissibility.

In the above technical solutions, the laser emitting unit and the laser receiving unit are provided at two sides of the transmission device respectively, and the transmissibility of the laser beam relative to the substrate may be calculated by irradiating the substrate by the laser beam, so that the line width of the black matrix in the substrate may be calculated based on the transmissibility, and thus it is determined whether the line width of the black matrix meets the requirement. Thus, the line width of the matrix in each substrate to be inspected on the transmission device may be inspected without stopping the transmission device, and the line width of the black matrix may be calculated in a prompt and precise manner based on the transmissibility.

In the present disclosure, unless otherwise explicitly indicated, the term "plurality of" means two or more than two.

The above are merely the preferred embodiments of the present disclosure and shall not be used to limit the scope of the present disclosure. It should be noted that, a person skilled in the art may make improvements and modifications without departing from the principle of the present disclosure, and these improvements and modifications shall also fall within the scope of the present disclosure.

What is claimed is:

1. A substrate inspection method, comprising:
   emitting, by a laser emitter, a laser beam to a substrate to be inspected at one side of the substrate to be inspected;
   receiving, by a laser receiver, the laser beam transmitted through the substrate to be inspected at the other side of the substrate to be inspected;
   moving the substrate continuously during inspection; and
   calculating transmissibility relative to the substrate to be inspected based on the emitted laser beam and the received laser beam, and determining whether a line width of a black matrix in the substrate to be inspected is within a predetermined range of the line width based on the transmissibility,
   wherein the method further comprising:
   determining whether the transmissibility is within a predetermined range of the transmissibility; if not, determining that the line width of the black matrix in the substrate to be inspected is not within the predetermined range of the line width; and if yes, determining that the line width of the black matrix in the substrate to be inspected is within the predetermined range of the line width.

2. The substrate inspection method according to claim 1, wherein the predetermined range of the line width is obtained by inspecting a predetermined position of a standard substrate by a user.

3. The substrate inspection method according to claim 2, wherein the predetermined position is same as the inspecting position of the substrate to be inspected.

4. The substrate inspection method according to claim 2, further comprising:
   controlling movements of the laser emitter and the laser receiver based on an exposed area of the substrate to be inspected, and controlling a position where the laser emitter emits the laser beam.

5. The substrate inspection method according to claim 4, further comprising:
   controlling the substrate to stop moving when it is determined that the line width of the black matrix in the substrate to be inspected is not within the predetermined range of the line width.

6. The substrate inspection method according to claim 4, wherein the substrate to be inspected comprises a plurality of exposed areas, the method further comprises:

controlling the laser emitter and the laser receiver to reciprocate in a direction perpendicular to a direction in which the substrate moves, and controlling the laser emitter to emit the laser beam upon moving to the predetermined position in each of the plurality of exposed areas in the substrate to be inspected, and calculating the transmissibility relative to each of the plurality of exposed areas, and calculating the transmissibility relative to the substrate to be inspected based on the transmissibility of each of the plurality of exposed areas.

7. The substrate inspection method according to claim 4, wherein the substrate to be inspected comprises four exposed areas, the method further comprises:

controlling the laser emitter and the laser receiver to move to any three exposed areas in the substrate to be inspected, and controlling the laser emitter to emit the laser beam upon moving to the predetermined position in each of the three exposed areas, and calculating the transmissibility of each of the exposed areas, and calculating the transmissibility of the substrate to be inspected based on the transmissibility of each of the three exposed areas.

8. The substrate inspection method according to claim 1, further comprising:

converting the transmissibility into the line width of the black matrix in the substrate to be inspected, and determining whether the line width of the black matrix is within the predetermined range of the line width.

9. The substrate inspection method according to claim 8, wherein the line width of the black matrix=$A \times (-\log$ (a value of the transmissibility))+$B$, wherein both A and B are constants.

10. The substrate inspection method according to claim 9, further comprising:

setting the constants A, B and/or the predetermined range of the line width according to a received instruction.

11. The substrate inspection method according to claim 1, further comprising:

sending an alert message, by an alert, when it is determined that the line width of the matrix in the substrate to be inspected is not within the predetermined range of the line width.

12. A substrate inspection method, comprising:

emitting, by a laser emitter, a laser beam to a substrate to be inspected at one side of the substrate to be inspected;

receiving, by a laser receiver, the laser beam transmitted through the substrate to be inspected at the other side of the substrate to be inspected;

moving the substrate continuously during inspection; and calculating transmissibility relative to the substrate to be inspected based on the emitted laser beam and the received laser beam, and determining whether a line width of a black matrix in the substrate to be inspected is within a predetermined range of the line width based on the transmissibility, wherein the method further comprising:

converting the transmissibility into the line width of the black matrix in the substrate to be inspected, and determining whether the line width of the black matrix is within the predetermined range of the line width, the line width of the black matrix=$A \times (-\log$ (a value of the transmissibility))+$B$, wherein both A and B are constants.

13. The substrate inspection method according to claim 12, further comprising:

setting the constants A, B according to a received instruction.

14. The substrate inspection method according to claim 12, further comprising:

sending an alert message, by an alert, when it is determined that the line width of the matrix in the substrate to be inspected is not within the predetermined range of the line width.

15. The substrate inspection method according to claim 12, further comprising:

controlling movements of the laser emitter and the laser receiver based on an exposed area of the substrate to be inspected, and controlling a position where the laser emitter emits the laser beam.

16. The substrate inspection method according to claim 15, further comprising:

controlling the substrate to stop moving when it is determined that the line width of the black matrix in the substrate to be inspected is not within the predetermined range of the line width.

17. The substrate inspection method according to claim 15, wherein the substrate to be inspected comprises a plurality of exposed areas, the method further comprises:

controlling the laser emitter and the laser receiver to reciprocate in a direction perpendicular to a direction in which the substrate moves, and controlling the laser emitter to emit the laser beam upon moving to a predetermined position in each of the plurality of exposed areas in the substrate to be inspected, and calculating the transmissibility relative to each of the plurality of exposed areas, and calculating the transmissibility relative to the substrate to be inspected based on the transmissibility of each of the plurality of exposed areas.

18. The substrate inspection method according to claim 15, wherein the substrate to be inspected comprises four exposed areas, the method further comprises:

controlling the laser emitter and the laser receiver to move to any three exposed areas in the substrate to be inspected, and controlling the laser emitter to emit the laser beam upon moving to a predetermined position in each of the three exposed areas, and calculating the transmissibility of each of the exposed areas, and calculating the transmissibility of the substrate to be inspected based on the transmissibility of each of the three exposed areas.

* * * * *